United States Patent
Weiss et al.

(10) Patent No.: US 7,184,575 B2
(45) Date of Patent: Feb. 27, 2007

(54) SEED TRAY FOR DIGITAL IMAGE ANALYSIS OF GRAIN AND THE LIKE

(75) Inventors: Marvin Weiss, Branford, CT (US); Bruce Armstrong, Kingston (AU)

(73) Assignee: Weiss Enterprises Inc., Branford, CT (US)

(*) Notice: Subject to any disclaimer, the term of this patent is extended or adjusted under 35 U.S.C. 154(b) by 664 days.

(21) Appl. No.: 10/217,264

(22) Filed: Aug. 9, 2002

(65) Prior Publication Data

US 2004/0052398 A1    Mar. 18, 2004

(51) Int. Cl.
*G06K 9/00* (2006.01)
(52) U.S. Cl. .................................. 382/110; 382/312
(58) Field of Classification Search ............... 382/110; 348/89, 91
See application file for complete search history.

(56) References Cited

U.S. PATENT DOCUMENTS

| | | | | |
|---|---|---|---|---|
| 4,818,383 A | * | 4/1989 | Wang | .......................... 209/702 |
| 4,975,863 A | * | 12/1990 | Sistler et al. | ................. 382/110 |
| 5,321,764 A | * | 6/1994 | Cullen et al. | ................. 382/110 |
| 5,917,927 A | * | 6/1999 | Satake et al. | ................. 382/110 |
| 2003/0048927 A1 | * | 3/2003 | Sato et al. | ................... 382/110 |

* cited by examiner

*Primary Examiner*—Joseph Mancuso
*Assistant Examiner*—Yuzhen Ge
(74) *Attorney, Agent, or Firm*—Bachman & LaPointe, P.C.

(57) ABSTRACT

A tray is provided for positioning objects for digital analysis wherein the objects have two ends defining a length, two edges defining a width and two side surfaces defining a thickness, wherein the tray includes a support surface defined in a plane and having at least one edge pocket adapted to position an object with one of the two edges facing upward for obtaining an image depicting thickness and length of the object, and having at least one side pocket adapted to position an object with one of the two side surfaces facing upward for obtaining an image depicting width and length of the object.

16 Claims, 5 Drawing Sheets

SEED TRAY FOR DIGITAL IMAGE ANALYSIS OF GRAIN AND THE LIKE

BACKGROUND OF THE INVENTION

The invention relates to evaluation of grain-like objects and, more particularly, to a tray for positioning of grain-like objects for digital analysis of same.

There are many types of grain and it is, undoubtedly, the most widely grown agricultural product. Grain is the most important direct staple food for most of mankind. Indirectly, grain is the basis for most animal husbandry. The plentiful availability of grain is the basis for providing most of our meat, poultry and fish at a reasonable cost.

Many measures are made to describe grain quality. High quality grain is fully grown and plump. It contains a full measure of protein. To permit storage for long periods of time, the grain must be sufficiently dry. Further, the grain must be free of numerous defects that can afflict it.

Measurement of grain quality must be done accurately and rapidly. During harvest time, huge quantities of grain are transferred from farmers to grain merchants in a short period of time. The quality of a truck load of grain, and hence the price of the grain, must be measured rapidly. The grain may not meet the quality requirements for human consumption but can be used as animal feed. In this case, the price will be lower. Some defects, such as ergot, which is a poisonous infection, may make the grain entirely useless.

There is therefore a very strong need for rapid and efficient testing methods for grain. Many instruments are available for this purpose. Infrared light instruments are used to obtain moisture and protein measurements. The size of grain kernels is traditionally measured using precise sieves through which the grain is passed thus dividing it into size fractions. The distribution of these size fractions is a measure of grain quality. However, this can be a time consuming process and is not useful for rapid quality measurement.

Despite the foregoing, for many instances, there are not readily available instruments, and quality must be established visually. In such measurement, examiners are trained in recognizing and assessing such defects as black point, smut and ergot. Such examiners are also trained to visually identify grain that has been damaged by too much or not enough rain or extreme temperatures as well. Of course, in this instance, the evaluation of grain quality requires an individual visual inspection, which can not be completed as rapidly as desired, and such methods lead to potentially different evaluation of the same loads of grain based upon subjective determinations made by the examiners.

U.S. Pat. No. 6,418,180, issued Jul. 9, 2002 to Weiss, discloses a method for digital analysis of objects such as grain, and provides an excellent method for obtaining rapid evaluation of the same. In connection with such digital analysis, however, it is desirable for the grain to be properly positioned relative to the apparatus which obtains the digital image.

It is therefore the primary object of the present invention to provide a tray for properly positioning objects for such digital analysis.

It is a further object of the present invention to provide such a tray whereby objects can be positioned to allow digital analysis of all aspects of the object.

It is a further object of the present invention to provide a method utilizing such a tray to obtain a digital image of such objects.

Other objects and advantages of the present invention will appear hereinbelow.

SUMMARY OF THE INVENTION

In accordance with the present invention, the foregoing objects have been readily attained.

According to the invention, a tray is provided for positioning objects for digital analysis, wherein said objects have two ends defining a length, two edges defining a width and two side surfaces defining a thickness, wherein the support member comprises a support surface defined in a plane and having at least one edge pocket adapted to position an object with one of said two edges facing upward for obtaining an image depicting thickness and length of said object, and having at least one side pocket adapted to position an object with one of said two side surfaces facing upward for obtaining an image depicting width and length of said object.

The tray in accordance with the present invention may advantageously further include at least one end-on hole for positioning an object with one end facing upward for obtaining an image depicting thickness and width of the object, as well as the end of the object.

In further accordance with the present invention, a method is provided for obtaining an image of length, width and thickness of objects, which method comprises the steps of providing a support member comprising a support surface defined in a plane and having at least one edge pocket adapted to position an object with one of said two edges facing upward for obtaining an image depicting thickness and length of said object, and having at least one side pocket adapted to position an object with one of said two side surfaces facing upward for obtaining an image depicting width and length of said object; positioning said objects on said support member so as to position said objects in said at least one edge pocket and said at least one side pocket; and obtaining an image of said objects on said support member.

BRIEF DESCRIPTION OF THE DRAWINGS

A detailed description of preferred embodiments of the present invention follows, with reference to the attached drawings, wherein:

FIG. 9 is a side view of the wide pocket of FIG. 8a;

FIG. 11 illustrates a side view of the end-on hole of FIG. 10a; and

DETAILED DESCRIPTION

The invention relates to a tray for positioning of objects for digital analysis. More particularly, the invention relates to a tray for positioning objects such as grains, seeds and the like, for digital analysis such as that described in U.S. Pat. No. 6,418,180, wherein the tray advantageously positions objects for obtaining a digital image which includes images for measuring length, width and thickness of the objects, and also for viewing ends, sides and edges of the objects.

Figure 1:
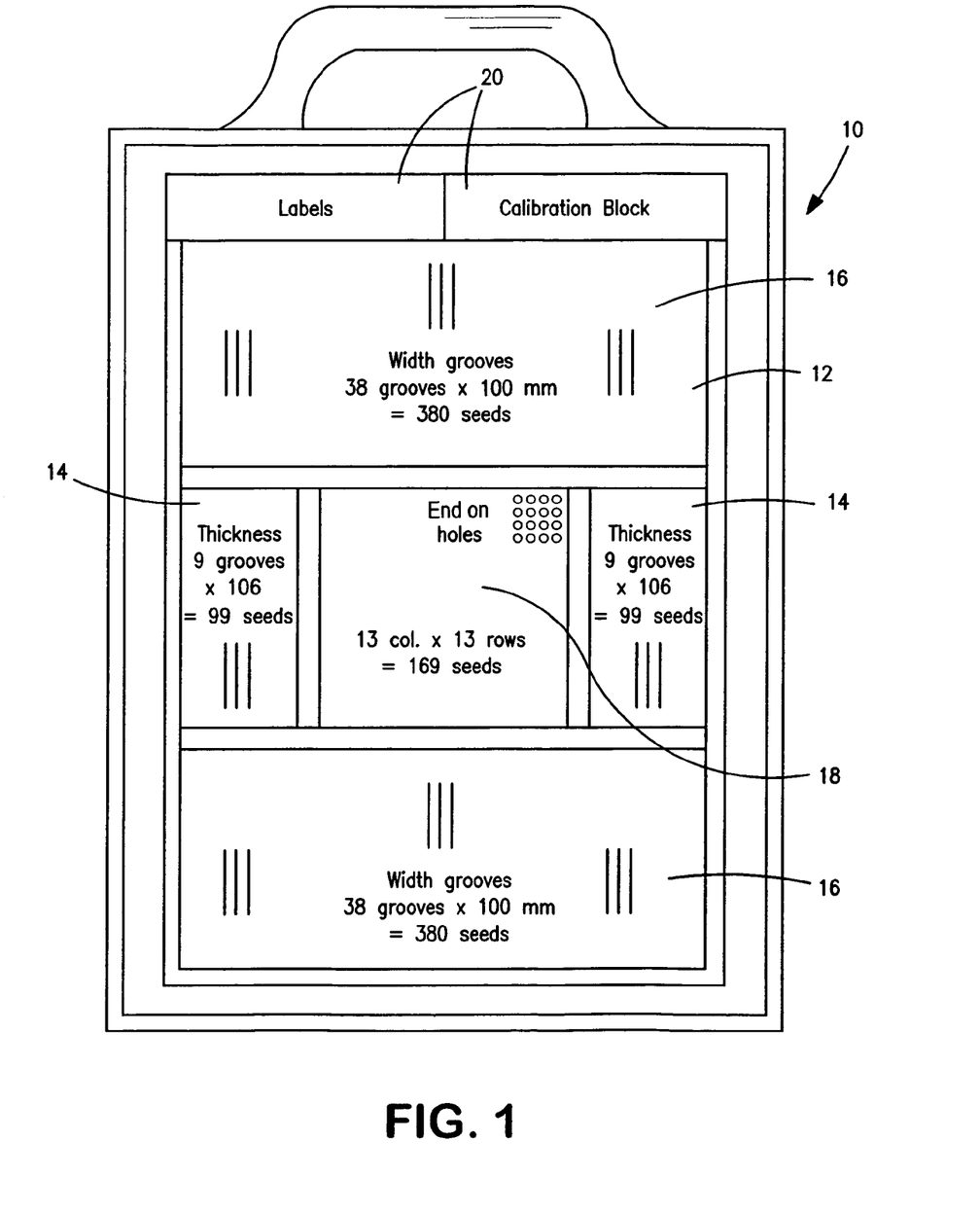
FIG. 1 schematically illustrates a top view of a tray in accordance with the present invention.

FIG. 1 schematically illustrates tray 10 in accordance with the present invention. Tray 10 is used to support a plurality of objects, such as grain, barley seeds and the like, and then a digital image is obtained of the tray holding such objects. The digital image can then be analyzed using known techniques, which may be incorporated into software and performed by a processing device such as a desktop computer and the like, to obtain an analysis of the quality of the grain, as well as any defects which may be present therein.

FIG. 1 therefore shows tray 10 having a substantially planar support surface 12 which is in the embodiment of FIG. 1 divided into several sections containing different structures. Specifically, support surface 12 preferably includes a plurality of edge pockets or thickness grooves, in this embodiment positioned in sections 14, a plurality of side pockets or width grooves positioned in sections 16, a plurality of end-on holes located in section 18, and a portion 20 for labels, calibration blocks and the like. In accordance with the present invention, tray 10 is advantageously provided having support surface 12 including at least two of the three types of sections 14, 16, 18 as described above, and may further advantageously have all three sections.

Figure 2:
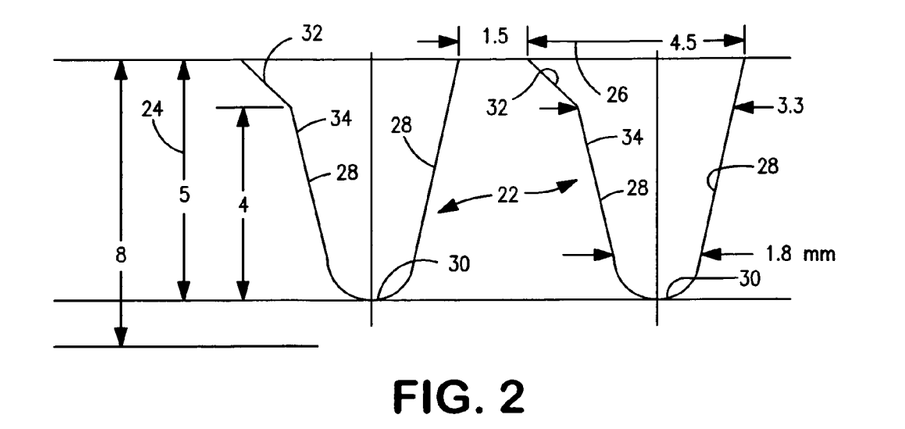
FIG. 2 schematically illustrates a side view of edge or narrow pockets in accordance with the present invention.
Figure 3:
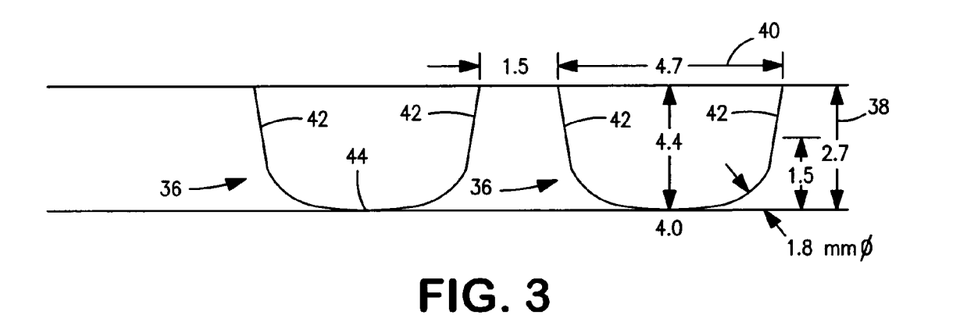
FIG. 3 schematically illustrates a side view of wide or side pockets in accordance with the present invention.
Figure 4:
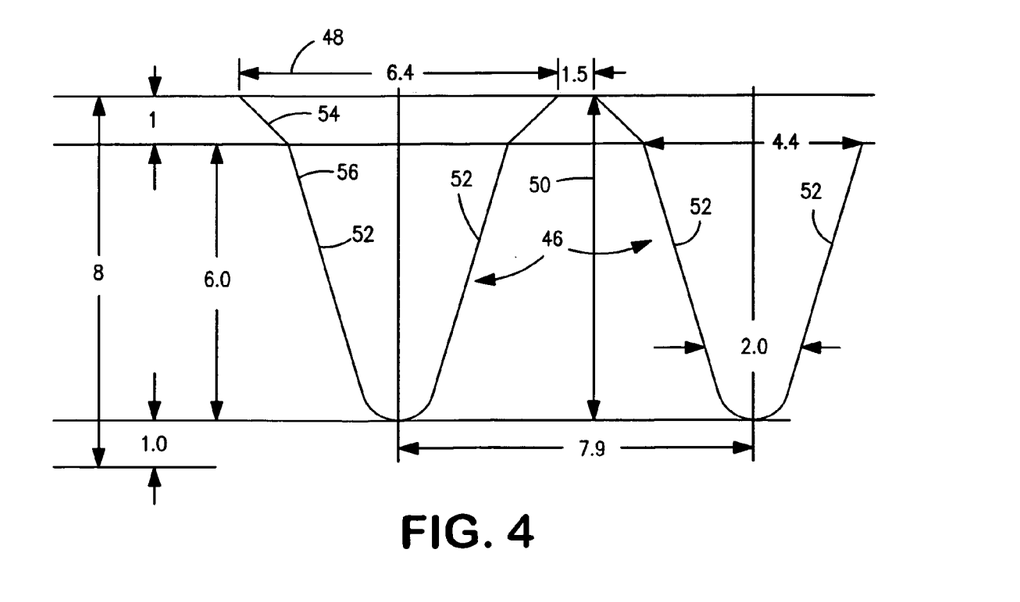
FIG. 4 schematically illustrates a side view of end-on holes or pockets in accordance with the present invention.

Referring to FIGS. 2–4, desirable structure for edge pockets, side pockets and end-on holes are further illustrated.

FIG. 2 shows a desirable structure for edge pockets 22 in accordance with the present invention, and shows such edge pockets having a depth 24 and a width 26, with edge pockets being defined by upwardly diverging walls 28 such that width 26 decreases from surface 12 down to the bottom 30 of pocket 22.

Still referring to FIG. 2, at least one of walls 28 can advantageously be provided having an upper portion 32 which is angled at relatively shallow angle relative to surface 12, and a bottom portion 34 which extends downwardly from top portion 32 and which is angled more steeply than top portion 32, relative to surface 12. This advantageously serves to guide objects such as grain and the like into the desired positioned within edge pocket 22 as desired. Further, bottom 30 of edge pockets 22 is advantageously a rounded bottom substantially as illustrated.

Turning to FIG. 3, an illustration of preferred structure of side pockets or thickness grooves 36 is provided. Side pockets 36 also have a depth 38 and a width 40, and are defined by walls 42. For side pockets 36, width 40 is advantageously greater than width 26 of edge pockets 22, and is further preferably sufficiently large as to accept the width of an object therein. Side pockets are designed in this manner such that an object is positioned therein on one side surface thereof such that width of the object can be determined.

Still referring to FIG. 3, walls 42 of side pockets 36 may also be provided diverging upwardly, but such divergence does not need to be to as great an extent as the divergence of edge pockets 22.

Further, bottom 44 of side pockets 36 is also advantageously elliptical in shape as shown.

Turning now to FIG. 4, the structure of end-on holes 46 is further illustrated. As shown, end-on holes 46 are preferably provided having a width 48 and depth 50 which are selected and adapted to position objects with one end thereof facing upwardly. Thus, end-on holes 46 in accordance with the present invention are preferably defined by upwardly diverging walls 52, and walls 52 may advantageously have a top portion 54 which is angled at a relatively shallow angle relative to surface 12, and a bottom portion 56 extending downwardly from top portion 54, and angled at a relatively steep slope relative to support surface 12.

FIGS. 2–4 further illustrate specific sizes for the various pockets and holes in accordance with the present invention, which sizes are a single embodiment that would advantageously serve for proper positioning of barley seeds. Thus, as shown in the drawings, edge pockets 22 may advantageously be provided having a space of 1.5 mm. between side edges thereof, and each edge pocket 22 may advantageously have a maximum width at surface 12 of 4.5 mm., and a width at the bottom of walls 28 of approximately 1.8 mm. Further, the width of edge pocket 22 at the transition point between top portion 32 and bottom portion 34 may advantageously be 3.3 mm. In connection with the depth of edge pockets 22, the total pocket may have a depth of approximately 5 mm., and the depth measured from the transition point between top portion 32 and bottom portion 34 to bottom 30 thereof may advantageously be approximately 4 mm. In this embodiment, the total thickness of tray 10 may be approximately 8 mm.

FIG. 3 shows preferred dimensions, in accordance with this embodiment, for side pockets 36. As shown, side pockets 36 may also be spaced from each other by a distance of about 1.5 mm, and may have a depth of about 2.7 mm. The width of side pockets 36 may advantageously in this embodiment be about 4.7 mm, and may decrease to approximately 4.0 mm at bottom 44 thereof.

FIG. 4 shows a preferred embodiment of end-on holes 46 wherein the holes have a maximum width of about 6.4 mm, and are spaced from each other by a spacing of 1.5 mm. Further, width of end-on holes 46 is narrower at the transition point between top portion 54 and bottom portion 56, and may advantageously be about 4.5 mm. Total depth of end-on holes 46 may advantageously be about 7.0 mm, with top portion 54 having a depth of about 1 mm, and bottom portion 56 having a depth of about 6.0 mm. These shapes and dimensions can be varied to suit any type of granular material. Edge pockets 22 and side pockets 36 may be provided having an elongate groove shape as schematically illustrated in FIG. 1. Alternatively, these structures may be defined in support surface 12 as discreet shapes intended to hold a single object.

Figure 5:
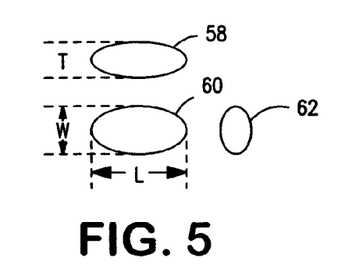
FIG. 5 schematically illustrates grains as typical objects to be analyzed in accordance with the present invention.

FIG. 5 illustrates several grains or barley seeds including a first grain 58 positioned on an edge thereof for measurement of a thickness T thereof, while grain 60 is positioned on a side surface for measurement of a width W thereof. Object 62 is positioned on an end, and can be used to measure both width and thickness. Further, objects 58, 60 in FIG. 5 are also positioned for measurement of a length L thereof.

Turning to FIGS. 6a–c and 7a–c, positioning of an object in a side pocket 36 is further illustrated. In this embodiment, side pockets 36 are discreet structures, rather than the grooves of FIG. 1, and therefore have a length, as well as a width and depth, wherein the length is selected to be greater than the expected length of objects to be positioned therein.

Figure 6A:
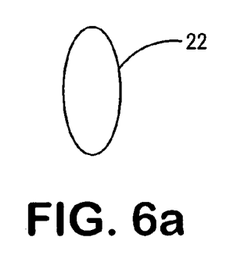
FIGS. 6a–c illustrate an edge pocket in accordance with the present invention and positioning of small and large grains in same.
Figure 6B:
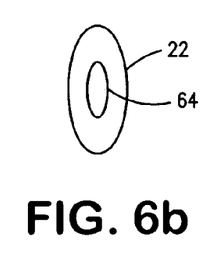
Figure 6C:
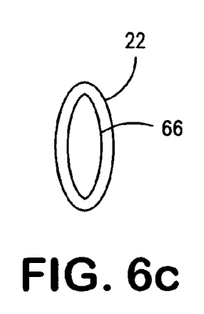
Figure 7A:
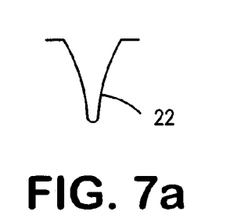
FIGS. 7a–c illustrate a side view of an edge pocket in accordance with the present invention holding a small and large grain in accordance with the present invention.
Figure 7B:
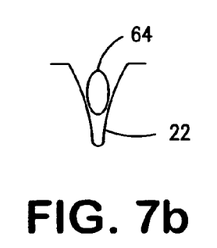
Figure 7C:
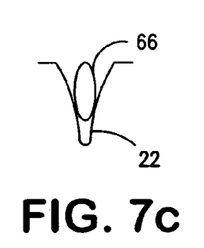

FIG. 6a shows an empty edge pocket 22, while FIG. 6b illustrates edge pocket 22 holding a small object 64, and FIG. 6c illustrates edge pocket 22 holding a relatively large object 66. As illustrated in FIGS. 7a–c, the diverging nature of walls 28, and size of upper and lower opening, advantageously serve to guide objects 64, 66 of different sizes into the appropriate position for digital analysis.

Figure 8A:
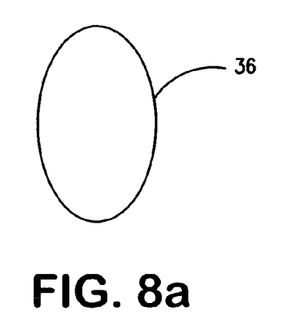
FIGS. 8a and 8b illustrate a top view of a wide or side pocket in accordance with the present invention holding a grain as desired.
Figure 8B:
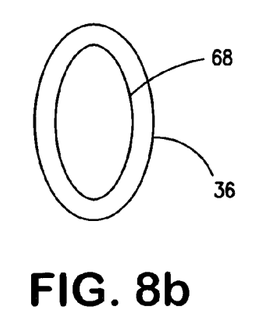
Figure 9:
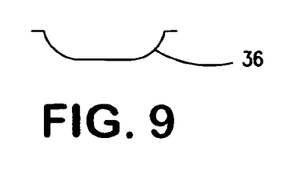

FIGS. 8a–b and 9 illustrate side pockets 36 and a grain 68 positioned therein for obtaining digital analysis of same. As shown, in this embodiment side pockets 36 are not grooves as illustrated in FIG. 1, but instead are discreet pockets having a length as well as a width and depth. As shown, side pockets 36 advantageously position grains or other objects 68 on a side surface thereof such that a digital image obtained from above object 68 will accurately depict both width and length of object 68 as desired.

Figure 10A:
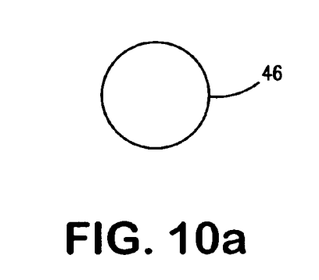
FIGS. 10a and 10b illustrate an end-on hole in accordance with the present invention containing a grain positioned as desired.
Figure 10B:
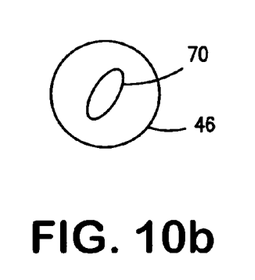
Figure 11:
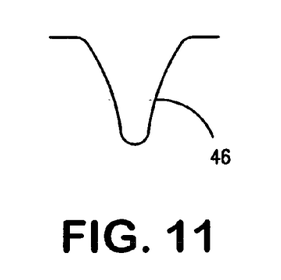

Turning now to FIGS. 10a–b and 11, the structure of a preferred embodiment of end-on holes 46 will be further discussed. FIG. 10a shows an end-on hole 46 and FIG. 10b shows end-on hole 46 containing a grain 70 positioned with one end facing upwardly for digital analysis, as desired, such that width and thickness of object 70 can be determined, and the end of grain 70 can also be analyzed for defects and the like.

FIG. 11 shows a side view of end-on hole 46 having upwardly diverging walls as discussed above in connection with FIG. 4.

In accordance with the present invention, and advantageously, the pockets 22, 36 in accordance with the present invention have a shape that advantageously permits seeds to fall into them and hold them as desired on their edges and side surfaces respectively.

In use, a sample of objects such as barley seeds are placed on tray 10 and advantageously are brushed back and forth preferably using a soft brush. This helps to guide the objects into pockets and holes and position them as desired so that thickness can be measured directly from objects located in edge pockets 22, and width can be measured directly from objects positioned in side pockets 36. Such a method can yield results equivalent to sieving, but which are not subject to the inherent error when human-measurement is used.

End-on holes 46 advantageously have a shape that permits the seeds to fall into them and be held vertically.

It should be appreciated that the spacing of pockets as described above advantageously serves to prevent objects such as grains and the like from touching each other prior to obtaining a digital image, as well, which further enhances the accuracy of all measurements obtained thereby.

In accordance with one embodiment of the present invention, tray 10 may be provided having a plurality of each of the types of pockets and holes as described. In accordance with one preferred embodiment of the present invention, tray 10 can be provided having side pockets 36 arranged in five columns, with 22 seeds being held in each column, for a total of 110 seeds in the side pockets. End-on holes may be positioned in tray 10 in six columns each containing 17 seeds, which will provide positions for an additional 102 seeds, while edge pockets 22 may further advantageously be provided in five columns, with each column holding 22 seeds, to also hold 110 seeds in these pockets. In such an embodiment, the pockets and holes in combination can hold 322 seeds, and a full tray can hold approximately 700 seeds. Thus, from a relatively small sample of seeds, a relatively large number of seeds can advantageously be positioned for proper digital analysis as desired.

Figure 12:
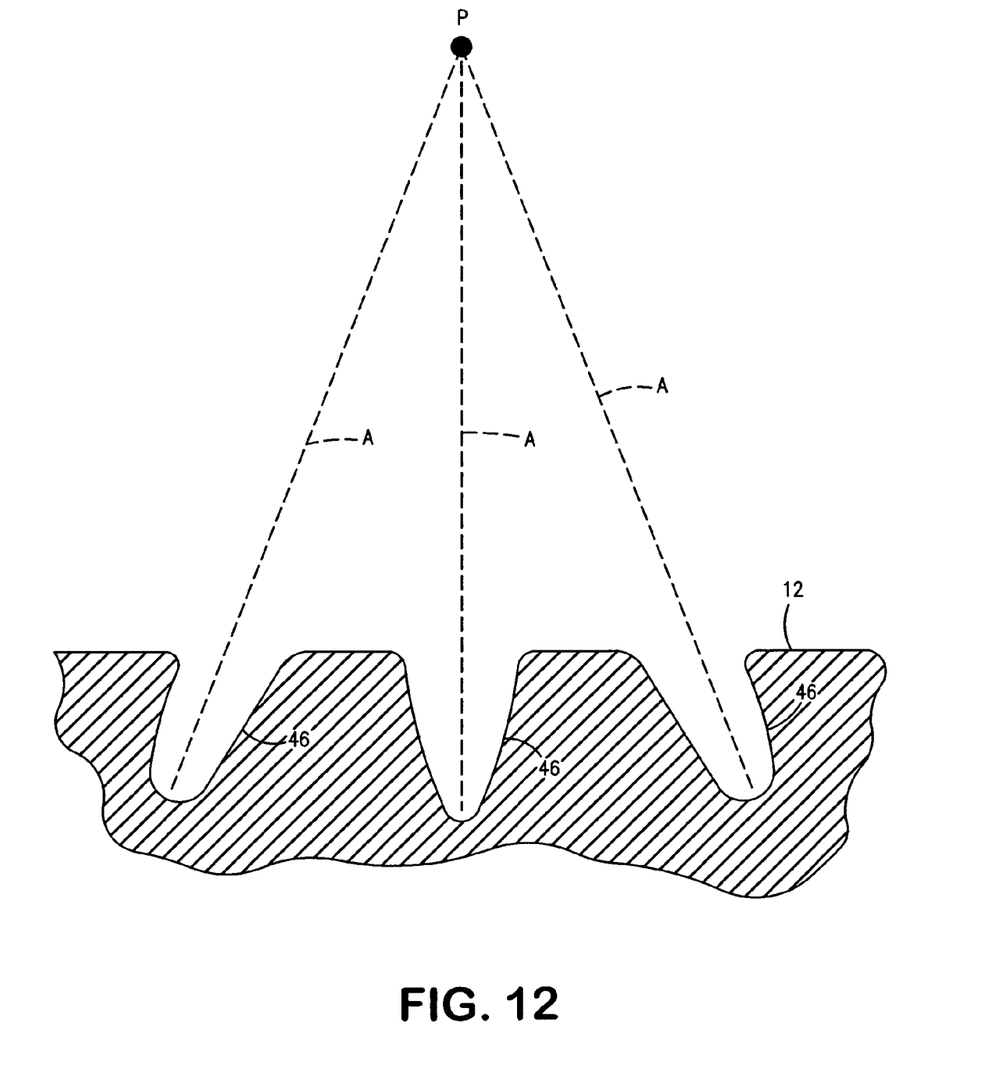
FIG. 12 is a side view of an alternate embodiment of the invention wherein a plurality of end-on holes have longitudinal axes A which converge to a focal point P.

In accordance with a further aspect of the present invention, digital images are typically obtained from a single lens or focal point. In this regard, images of grains in some pockets or holes may be obtained at an angle which is not perpendicular to support surface 12. For edge pockets 22 and side pockets 36, this angle is not critical and does not sufficiently distort the image to be of importance. However, in connection with end-on holes 46, it may be preferred to position end-on holes 46 relative to surface 12 at different angles such that end-on hole 46 has an axis, and the axes of all end-on holes converge to a single focal point. This is illustrated in FIG. 12. This advantageously allows for direct images to be obtained without distortion due to angles.

The embodiment of FIG. 1 further shows a configuration of the present invention which reduces problems caused by the angling of end-on holes as described above. Note that end-on holes positioned in section 18 position such holes at a substantial center portion of tray 10, where angles relative to a camera or the like would be reduced in any event.

It should be appreciated that tray 10 in accordance with the present invention advantageously serves to position seeds or other objects for obtaining a digital image that can be subsequently analyzed, wherein the positioning advantageously allows for direct viewing of width, length and thickness of objects thereon. Further, providing images of the end portions of objects advantageously assists in identifying certain serious defects such as the diseases mentioned above.

It should be appreciated that although the preferred embodiment is presented in terms of a tray containing various pockets and holes for supporting seeds, that any suitable support member can be provided with such pockets and holes. For example, as a support member, such pockets and holes could be provided in a conveyor, or a platform, or any other suitable support surface, all of which are included in the scope of the present invention. Thus, any suitable structure for supporting seeds which can be adapted to have pockets and holes falls within the broad scope of a support member in connection with the present invention.

It is to be understood that the invention is not limited to the illustrations described and shown herein, which are deemed to be merely illustrative of the best modes of carrying out the invention, and which are susceptible to modification of form, size, arrangement of parts and details of operation. The invention rather is intended to encompass all such modifications which are within its spirit and scope as defined by the claims.

What is claimed is:

1. A support member for positioning objects for digital analysis, wherein said objects have two ends defining a length, two edges defining a width and two side surfaces defining a thickness, said support member comprising a support surface defined in a plane and having at least one edge pocket adapted to position an object with one of said two edges facing upward for obtaining an image depicting thickness and length of said object, and having at least one side pocket adapted to position an object with one of said two side surfaces facing upward for obtaining an image depicting width and length of said object, wherein said at least one edge pocket is narrower than said at least one side pocket.

2. The apparatus of claim 1, wherein said support member is a tray.

3. A support member for positioning objects for digital analysis, wherein said objects have two ends defining a length, two edges defining a width and two side surfaces defining a thickness, said support member comprising a support surface defined in a plane and having at least one edge pocket adapted to position an object with one of said two edges facing upward for obtaining an image depicting thickness and length of said object, and having at least one side pocket adapted to position an object with one of said two side surfaces facing upward for obtaining an image depicting width and length of said object, wherein said support surface further comprises at least one end-on hole adapted to position an object with one of said two ends facing upward for obtaining an image depicting thickness and width of said object.

4. The apparatus of claim 3, wherein said at least one edge pocket is narrower than said at least one side pocket.

5. The apparatus of claim 3, wherein said at least one end-on hole comprises a plurality of end-on holes having longitudinal axes, and wherein said longitudinal axes converge to a focal point.

6. A support member for positioning objects for digital analysis, wherein said objects have two ends defining a length, two edges defining a width and two side surfaces defining a thickness, said support member comprising a support surface defined in a plane and having at least one edge pocket adapted to position an object with one of said two edges facing upward for obtaining an image depicting thickness and length of said object, and having at least one side pocket different in shape from said edge pocket and adapted to position an object with one of said two side surfaces facing upward for obtaining an image depicting width and length of said object, wherein said edge pocket comprises a depression into said support surface having a width and a depth, and wherein said depth is greater than said width.

7. The apparatus of claim 6, wherein said width is defined by upwardly diverging walls whereby said width decreases in size from said support surface to a bottom of said edge pocket.

8. A support member for positioning objects for digital analysis, wherein said objects have two ends defining a length, two edges defining a width and two side surfaces defining a thickness, said support member comprising a support surface defined in a plane and having at least one edge pocket adapted to position an object with one of said two edges facing upward for obtaining an image depicting thickness and length of said object, and having at least one side pocket different in shape from said edge pocket and adapted to position an object with one of said two side surfaces facing upward for obtaining an image depicting width and length of said object, wherein said side pocket comprises a depression into said support surface having a width and a depth, and wherein said width is greater than said depth.

9. A method for obtaining an image of objects having two ends defining a length, two edges defining a width and two side surfaces defining a thickness, comprising the steps of:
providing a support member comprising a support surface defined in a plane and having at least one edge pocket adapted to position an object with one of said two edges facing upward for obtaining an image depicting thickness and length of said object, and having at least one side pocket adapted to position an object with one of said two side surfaces facing upward for obtaining an image depicting width and length of said object, wherein said at least one edge pocket is narrower than said at least one side pocket;

positioning said objects on said support member so as to position said objects in said at least one edge pocket and said at least one side pocket; and obtaining an image of said objects on said support member.

10. The method according to claim 9, wherein said support member is a tray.

11. A method for obtaining an image of objects having two ends defining a length, two edges defining a width and two side surfaces defining a thickness, comprising the steps of:
providing a support member comprising a support surface defined in a plane and having at least one edge pocket adapted to position an object with one of said two edges facing upward for obtaining an image depicting thickness and length of said object, and having at least one side pocket adapted to position an object with one of said two side surfaces facing upward for obtaining an image depicting width and length of said object; wherein said at least one edge pocket is narrower than said at least one side pocket;

positioning said objects on said support member so as to position said objects in said at least one edge pocket and said at least one side pocket; and obtaining an image of said objects on said support member, wherein said support surface further comprises at least one end-on hole adapted to position an object with one of said two ends facing upward for obtaining an image depicting thickness and width of said object.

12. A method according to claim 11, wherein said at least one edge pocket is narrower than said at least one side pocket.

13. A method according to claim 11, wherein said at least one end-on hole comprises a plurality of end-on holes having longitudinal axes, and wherein said longitudinal axes converge to a focal point.

14. A method for obtaining an image of objects having two ends defining a length, two edges defining a width and two side surfaces defining a thickness, comprising the steps of:
providing a support member comprising a support surface defined in a plane and having at least one edge pocket adapted to position an object with one of said two edges facing upward for obtaining an image depicting thickness and length of said object, and having at least one side pocket different in shape from said edge pocket and adapted to position an object with one of said two side surfaces facing upward for obtaining an image depicting width and length of said object;

positioning said objects on said support member so as to position said objects in said at least one edge pocket and said at least one side pocket; and obtaining an image of said objects on said support member, wherein said edge pocket comprises a depression into said support surface having a width and a depth, and wherein said depth is greater than said width.

15. A method according claim 14, wherein said width is defined by upwardly diverging walls whereby said width decreases in size from said support surface to a bottom of said edge pocket.

16. A method for obtaining an image of objects having two ends defining a length, two edges defining a width and two side surfaces defining a thickness, comprising the steps of:

providing a support member comprising a support surface defined in a plane and having at least one edge pocket adapted to position an object with one of said two edges facing upward for obtaining an image depicting thickness and length of said object, and having at least one side pocket different in shape from said edge pocket and adapted to position an object with one of said two side surfaces facing upward for obtaining an image depicting width and length of said object;

positioning said objects on said support member so as to position said objects in said at least one edge pocket and said at least one side pocket; and obtaining an image of said objects on said support member, wherein said side pocket comprises a depression into said support surface having a width and a depth, and wherein said width is greater than said depth.

* * * * *